United States Patent [19]

Lassen et al.

[11] Patent Number: 4,627,848

[45] Date of Patent: Dec. 9, 1986

[54] ANATOMICAL PAD

[75] Inventors: Frederich O. Lassen; Dianne S. Masten, both of Winnebago County; Cheri L. Schultz; Robert J. Peerenboom, both of Outagamie County, all of Wis.

[73] Assignee: Kimberly-Clark Corporation, Neenah, Wis.

[21] Appl. No.: 603,064

[22] Filed: Apr. 23, 1984

[51] Int. Cl.[4] .............................................. A61F 13/20
[52] U.S. Cl. .................................. 604/370; 604/378; 604/385 R
[58] Field of Search ............... 604/370, 374, 375, 378, 604/379, 384, 385, 372, 387, 367, 366

[56] References Cited

U.S. PATENT DOCUMENTS

| 810,135 | 1/1906 | Green | 604/378 |
|---|---|---|---|
| 2,238,450 | 4/1941 | Rabell | 604/379 |
| 2,964,039 | 12/1960 | Johnson et al. | 604/385 R |
| 3,143,113 | 8/1964 | Mills | 604/378 |
| 3,726,277 | 4/1973 | Hirschman . | |
| 3,865,112 | 2/1975 | Roeder | 604/387 |
| 4,100,324 | 6/1978 | Anderson et al. | 604/366 |
| 4,340,058 | 7/1982 | Pierce et al. | 604/372 |
| 4,460,642 | 6/1984 | Errede et al. | 604/367 |

FOREIGN PATENT DOCUMENTS

| 618787 | 4/1961 | Canada | 604/378 |
|---|---|---|---|
| 6707397 | 12/1967 | Netherlands | 604/378 |
| 410702 | 5/1936 | United Kingdom | 604/385 |
| 1424619 | 2/1976 | United Kingdom . | |
| 2073597 | 10/1981 | United Kingdom . | |

OTHER PUBLICATIONS

British-Search Report for Application No. 85-10268, May 29, 1985 (1 page).

Primary Examiner—Dalton L. Truluck
Assistant Examiner—Karen L. Kaechele
Attorney, Agent, or Firm—Paul A. Leipold; D. L. Traut; J. J. Duggan

[57] ABSTRACT

An anatomical liner is provided which is ellipsoidal in both horizontal and vertical cross-section and is designed to be positioned and maintained within the vulva without penetrating the vaginal canal.

30 Claims, 6 Drawing Figures

ANATOMICAL PAD

BACKGROUND OF THE INVENTION

This invention relates to a novel sanitary protection device and particularly to an anatomical liner which is held in position by body morphology and does not need external attachment means.

FIELD OF THE INVENTION

Both traditional forms of feminine hygiene protection suffer from disadvantages. Tampons may present insertion and withdrawal problems, are difficult and messy to handle at times and may be limited in use because of health problems. Sanitary napkins on the other hand, can be cumbersome, and compared to tampons, are bulky and after extended wear may chafe the thighs of the wearer. In addition, very little of the absorbent material present in the sanitary napkin is actually utilized. Further, due to the bulk and configuration of the napkin it may be visible under certain tight fitting clothes.

Because of the problems inherent with both napkins and tampons several attempts have been made to produce products which appear to be combinations of both and are characterized generally by a raised projection designed to extend upward into the vagina in combination with a napkin which may be of reduced size but is otherwise essentially conventional. Other sanitary napkins have been made which provide raised central portions for increased absorbency. These napkins are generally conventional in size and configuration except for the raised area and require the use of garment attachment adhesive to maintain their position with respect to the garment. The problem with these napkins as with conventional napkins, is movement distorts the napkin configuration which is bound to move in conjunction with the garment rather than the body. This provides for discomfort and premature leakage due to distortion of the profile of the napkin adjacent the vulva. Other attempts at designing more comfortable pads have been those relating to reducing size, both in the areas of thickness and length but the same distortion problems occur and even while there is enough absorbent present, generally, in these reduced size pads the absorbent is not fully utilized. Representative of prior art illustrating the concepts described above are U.S. Pat. Nos. 2,331,355; 4,079,739; 3,115,877; 3,756,232; 3,570,491; 3,993,074; 2,964,039; 3,339,208; 4,072,151; 2,328,795; 2,917,049; 2,629,381; 2,682,875; 2,917,049; 3,726,277; 3,983,873; 4,095,542; 3,528,422; 2,104,423; British Nos. 289,101 and 855,537; and French No. 2,420,339. It is believed that the above patents reflect the variety of approaches used to solve difficulties inherent in the previously available catamenial devices, but are not particularly relevant to the solution disclosed below.

U.S. Pat. No. 2,408,508 issued to Canavan discloses a nonchafing catamenial pad designed to conform to the contour with the "natural anatomical curves of the body in the region of the female genitalia . . . " and extends from a point slightly beyond the mons veneris to the anus. This pad is flat along a horizontal plane defining its top and bottom and has curved edges and ends with the pad tapering from a wide front end to a narrow back end adjacent the anus. According to the disclosure in this patent the length of the absorbent material is at least 6½ inches long with a folded wrapped gauze extension both a front and back to provide for attachment to a supporting belt. The gauze wrapper is folded several times at the bottom of the napkin to provide support to prevent bunching, twisting, and other distortion forces commonly associated with what is apparently a relatively flimsy napkin. U.S. Pat. No. 3,983,373 describes interlabial napkins of several symmetrical flat-sided configurations.

SUMMARY OF THE INVENTION

According to this invention an anatomical liner is provided which fits within the vulva at its leading edge and extends not greater than 6 inches in length due to the ellipsoidal configuration of the liner in both horizontal and vertical cross-section. The liner is preferably wider, thicker, and more rounded at the leading edge and the liner will stay in place without the use of garment attachment adhesive.

These napkins, which due to their shape, and dimensions, i.e., less than six inches long and preferably between one and two inches wide are designed to be worn externally to the vagina but within the limits of the vulva. The dimensions are based upon an analysis of female anatomy which indicates that the majority of women have a combined length of the labia minora and labia majora not greater than five inches. Since, optimally, the length of the pad will reflect the length of this combined measurement, it will nestle within the vulva and move only in response to body movements. The shape of the pad is designed to put the maximum amount of absorbent material in the area where it is most needed and, due to design features described subsequently, to maximize the efficiency of the absorbent so that the reduced length and width of the anatomical pad, when compared to sanitary napkins, will provide essentially the same functional capacity and, with the elimination of failure due to distortion, superior protection.

DETAILED DESCRIPTION OF THE INVENTION AND DRAWINGS

The invention may be more readily understood by reference to the drawings in which FIGS. 1–6 illustrate perspective views partially in cross section of different embodiments of the anatomical pad of this invention. It will be readily understood by those skilled in the art that each of these embodiments combine features which could be combined with features of other embodiments depending upon such other factors as cost and processability.

The unique geometry of each of these embodiments, however, allow the pads of this invention to nestle inconspicuously in the vulva without protrusions extending significantly beyond the front juncture of the labia majora while stopping at the rear juncture of the labia and without extending significantly into the perineum.

Figure 1:
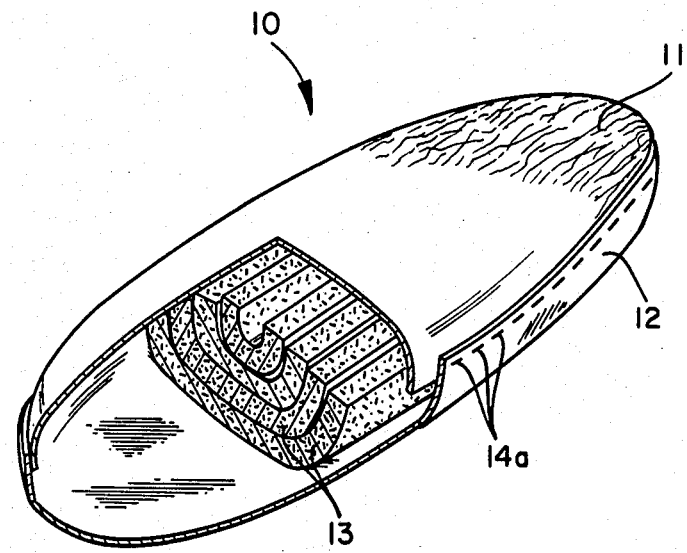

The least conspicuous of the anatomical pads of this invention as illustrated at FIG. 1 in which the pad 10 utilizes as an absorbent a series of U-shaped absorbent layers 13. The U-shaped absorbent layers takes advantage of a principle more fully described in U.S. patent application No. 472,708 of which I am the inventor. It has been found that when fibers forming a batt are turned 90° from the axis of deposition they more readily transmit fluid in the z direction. In other words, fibers which are traditionally layed in the xy, i.e., horizontal direction are rotated to provide an end profile beneath the source of fluid, fluid will rapidly be conveyed downward into the bottom of the batt.

This can be seen from FIG. 1, wherein a series of U-shaped absorbent layers are positioned in such a manner that several end profiles are provided adjacent the fluid pathway when the napkin is in use. This profile provides for minimum lateral wicking along the surface of the absorbent material and, substantial z-direction capillary attraction which minimizes the possibility of runoff along the cover 11.

Referring again to FIG. 1 the fluid impervious baffle 12 surrounds the bottom of the absorbent and the sides actually overlapping the cover 11 at the edge of the upper profile of the anatomical pad. Except as otherwise noted, the cover material is of a conventional type, i.e., nonwoven thermoplastic of the type used on sanitary napkins currently. Sealing between the cover and baffle may be by fusing which can be accomplished ultrasonically or by adhesive as is well known in the art. It is also contemplated to use a single material which forms both the cover and the baffle with the fluid impermeability added to the baffle by the addition of a suitable fluid impermeable film former such as latex.

Figure 2:
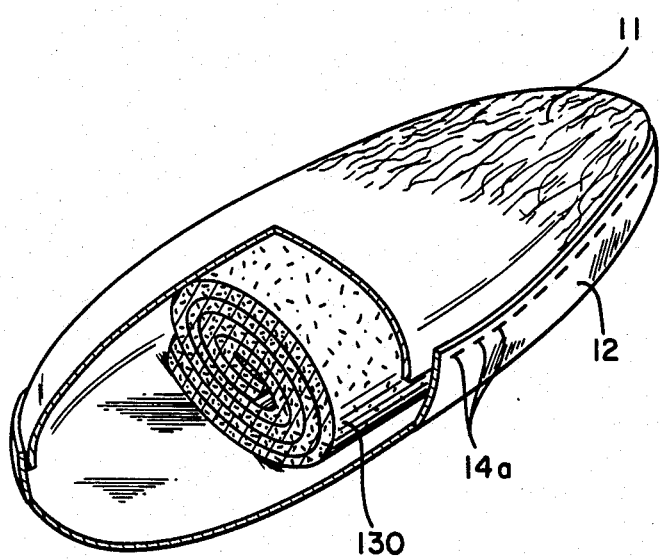

As can be seen in FIG. 2 the only difference between the embodiment depicted there and the one depicted in FIG. 1 is the difference in the shape of the absorbent core 130. The absorbent layer 130 is formed by creating a central capillary profile made by the juncture of two rolled absorbent webs with the xy orientation of the fibers in the absorbent webs acting in consort to collect the fluid and direct it from the surface downward into the depth of the pad.

Figure 3:
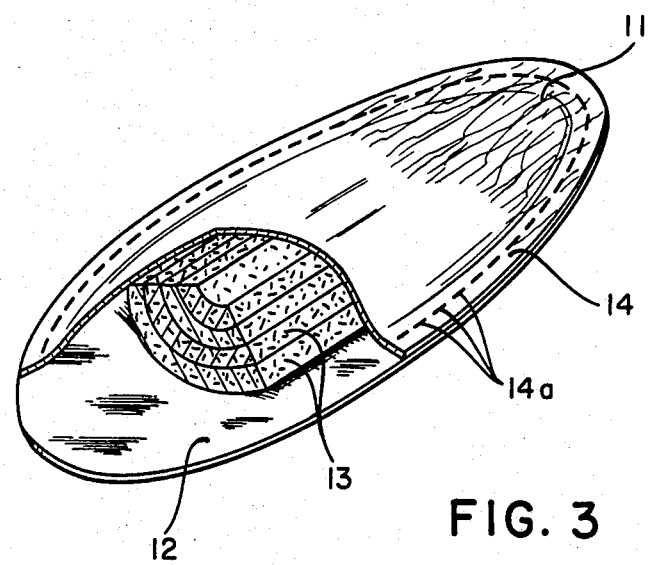
Figure 4:
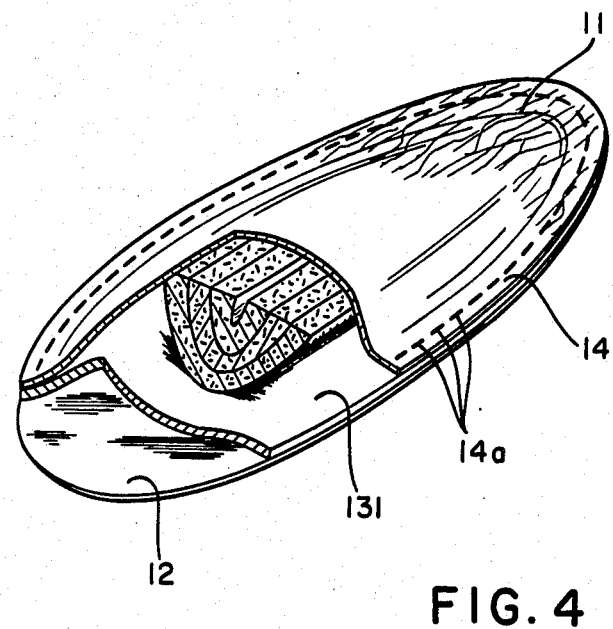

FIGS. 3 and 4 show variations in the horizontal configuration of this invention. In these embodiments, the cover and the bottom layers are joined externally within the center of the horizontal plane which bisects the pad as opposed to the embodiments depicted in FIGS. 1 and 2. The binding flange 14 may seal the anatomical pad by ultrasonic means as illustrated by spaced fused portions 14a positioned around the flange. This particular shape helps to give the anatomical pad added axial stability and tends to prevent the device from rolling circumferentially around the horizontal axis. The added width of the flange is about 0.5–0.25 inches and even with this additional width the anatomical pad does not reach the sensitive inner thigh area.

The configuration depicted in FIG. 4 shows an absorbent construction with several absorbent layers 131 arranged so that the central most reoriented layers are in direct fluid conductive contact with the bottom most portion of the pad.

Figure 5:
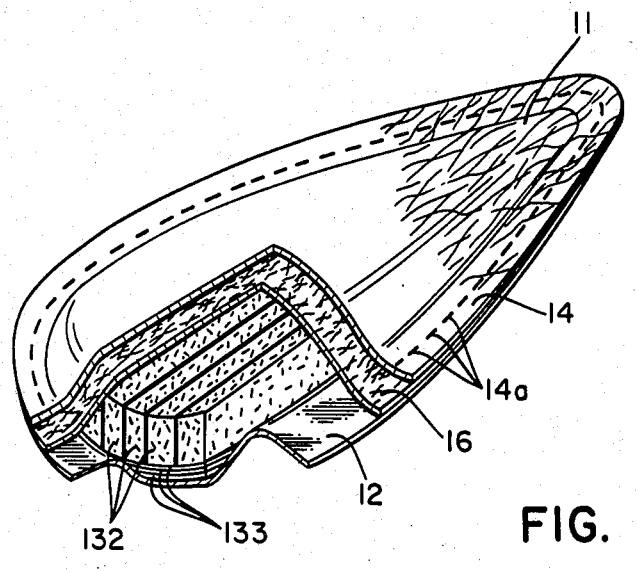
Figure 6:
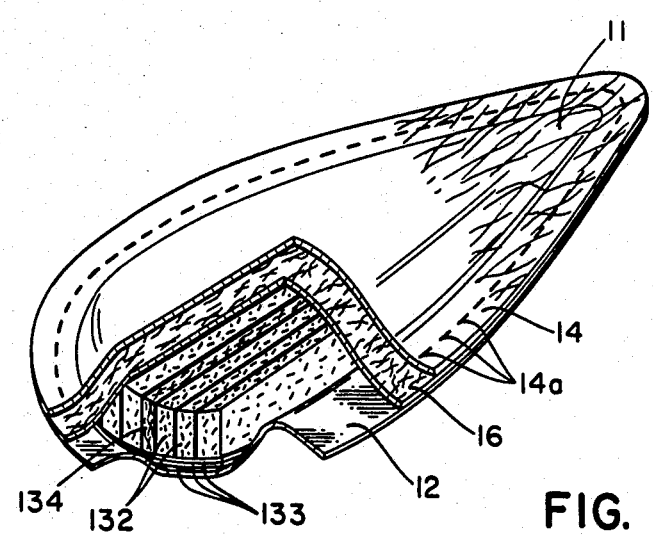

The embodiments depicted at FIGS. 5 and 6 depict napkins in which the trailing or distal end is elongated. This elongated somewhat thinner distal end profile combined with the oval contour of the pads vertical cross-section allows the pad to cover the vulva without contact of the edge with the inner thigh portion. The oval contour of the vertical cross-section also enables the pad to mold into the folds of the labia thus providing a seal against fluid leakage prior to pad saturation.

The tapered distal end provides for increasing comfort in an area where minimum absorbent capacity is needed. It should be emphasized that the taper is both horizontal and vertical in nature.

The embodiment depicted at FIG. 5 shows a pad with a multi-component internal absorbent system which includes a thin carded web adjacent the body cover. Immediately beneath the web is a transfer layer 132 composed of strips of a thermally bonded fibrous web containing 20–40% hydrophilic and 80–60% hydrophobic staple fibers which are again turned at 90° to the forming direction. This, as mentioned previously, provides for rapid fluid conduction in the z direction the presence of thermoplastic cover prevents a matrix of capillaries which do not collapse when wet. The absorbent surfactant treated microfiber layer 133 which is in essence several layers of thermobonded meltblown microfiber which has been treated with a surfactant to enable it to retain and wick fluid as described in U.S. Pat. No. 4,372,312 provides an extremely efficient system in combination with the 90° turned fibers for maximum fluid distribution and utilization.

The embodiment depicted at FIG. 6 is identical to that depicted at FIG. 5 except for the inclusion of a microfiber transfer layer 134 to help transfer the fluid downward as well as hold it in the absorbent core formed by the meltblown microfiber layer 133.

The utilization of the layers of absorbent which have been turned about their axis 90° is the only thing common about each of the embodiments depicted above. The rapid downward transmission of fluid aids in maintaining surface cover dryness as well as helping to completely utilize the absorbent material which, compared to a sanitary napkin is concentrated in an area of increased depth but substantially reduced planar surface.

The utilization of microfiber as a wicking and entrapment aid also provides for superior performance with limited volume and bulk.

It is also contemplated to selectively use finely divided particulate superabsorbent material which may be spaced throughout the 90° oriented layers or distributed throughout the meltblown microfiber webs per se.

It is preferred to incorporate a percentage up to 80% of hydrophobic staple fibers in the 90° reoriented web to maintain the capillary structure after wetting. Without substantial amounts of thermoplastic fibers being present in the web, the cellulosic fibers which tend to collapse when wet would in a short time inhibit the downward transmission of fluid.

A preferred mixture for the embodiments shown above of hydrophobic to hydrophilic fibers is 20–40% hydrophobic to 80–60% hydrophilic fibers.

What is claimed is:

1. An elongate anatomical pad having a leading end and a distal end with an absorbent matrix, a fluid pervious cover overlying said absorbent matrix and a fluid impermeable baffle surrounding the portion of the absorbent matrix opposite said cover said absorbent matrix being ellipsoidal in horizontal and in vertical cross section dimensioned to be positioned essentially completely within the vulva with said device not contacting vaginal walls within the vulva with said device not contacting vaginal walls after positioning wherein the oval contour of the pad's vertical cross section enables said pad to mold against the folds of the labia providing a seal against fluid leakage and wherein said pad comprises a series of U-shaped absorbent layers with their layer orientation such that the longitudinal axis of the U is in the same direction as the longitudinal axis of said pad and the ends of said U-shaped layers are adjacent said previous cover.

2. The anatomical liner of claim 1 wherein the leading end is wider at the front facing than the distal end.

3. The anatomical pad of claims 1 or 2 wherein the distal end is thinner and narrower than the leading end.

4. The anatomical pad of claim 1 wherein the absorbent contains surfactant treated meltblown microfiber.

5. The anatomical pad of claim 1 wherein a bonding flange extends peripherally around the horizontal axis which bisects the liner and is formed by the baffle and the cover.

6. The anatomical pad of claim 5 wherein the absorbent extends into the flange area.

7. The anatomical pad of claim 1 wherein the thickness of the liner is not greater than its width.

8. The anatomical pad of claims 1 and 7 wherein the length is not greater than six inches.

9. The pad of claim 8 wherein the width of said pad is between about 1 and about 2 inches.

10. The pad of claim 1 wherein said absorbent comprises a series of U-shaped absorbent layers.

11. The pad of claim 1 wherein said absorbent comprises about 20–40% hydrophobic fibers and 80–60% hydrophilic fibers.

12. The pad of claim 1 wherein said absorbent includes particulate superabsorbent material.

13. The pad of claim 1 wherein said pad is dimensioned to be positioned essentially completely within the vulva with said device not contacting vaginal walls after positioning.

14. An elongate anatomical pad having a leading end and a distal end with an absorbent matrix, a fluid pervious cover overlying said absorbent matrix and a fluid impermeable baffle surrounding the portion of the absorbent matrix opposite said cover said absorbent matrix being ellipsoidal in horizontal and in vertical cross section and wherein the oval contour of the pad's vertical cross section enables said pad to mold against the folds of the labia providing a seal against fluid leakage and wherein said absorbent matrix comprises rolled absorbent webs with their orientation such that the longitudinal axis of the roll is in the same direction as the longitudinal axis of said pad.

15. The anatomical liner of claim 14 wherein the leading end is wider at the front facing than the distal end.

16. The anatomical pad of claim 14 wherein the distal end is thinner and narrower than the leading end.

17. The anatomical pad of claim 14 wherein the absorbent contains surfactant-treated meltblown microfiber.

18. The anatomical pad of claim 14 wherein a bonding flange extends peripherally around the horizontal axis which bisects the liner and is formed by the baffle and the cover.

19. The anatomical pad of claim 14 wherein the length is not greater than six inches.

20. The pad of claim 17 wherein the width of said pad is between about 1 and about 2 inches wide.

21. An elongate anatomical pad having a leading end and a distal end with an absorbent matrix, a fluid pervious cover overlying said absorbent matrix and a fluid impermeable baffle surrounding the portion of the absorbent matrix opposite said cover said absorbent matrix being ellipsoidal in horizontal and in vertical cross section and wherein the oval contour of the pad's vertical cross section enables said pad to mold against the folds of the labia providing a seal against fluid leakage and wherein below said cover is a transfer layer composed of strips of a thermally-bonded fibrous web containing 20–40% hydrophilic and 80–60% hydrophobic staple fibers which are turned at 90° to the forming direction.

22. The anatomical liner of claim 21 wherein the leading end is wider at the front facing than the distal end.

23. The anatomical pad of claim 21 wherein the distal end is thinner and narrower than the leading end.

24. The anatomical pad of claim 21 wherein the absorbent contains surfactant-treated meltblown microfiber.

25. The anatomical pad of claim 24 wherein surfactant-treated meltblown microfiber is used for z direction fluid transfer.

26. The anatomical pad of claim 21 wherein a bonding flange extends peripherally around the horizontal axis which bisects the liner and is formed by the baffle and the cover.

27. The anatomical pad of claim 21 wherein the length is not greater than six inches.

28. The pad of claim 21 wherein the width of said pad is between about 1 and about 2 inches.

29. The pad of claim 21 wherein said pad is dimensioned to be positioned essentially completely within the vulva with said device not contacting vaginal walls after positioning.

30. The pad of claim 21 wherein said pad includes a thin carded web adjacent said previous cover.

* * * * *